(12) United States Patent
Hirose (10) Patent No.: US 8,851,673 B2
(45) Date of Patent: Oct. 7, 2014

(54) IMAGING APPARATUS (71) Applicant: Canon Kabushiki Kaisha, Tokyo (JP)

(72) Inventor: Futoshi Hirose, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/759,439

(22) Filed: Feb. 5, 2013

(65) Prior Publication Data

US 2013/0215384 A1  Aug. 22, 2013

(30) Foreign Application Priority Data

Feb. 21, 2012  (JP) ................ 2012-035089

(51) Int. Cl.
*A61B 3/14* (2006.01)
*A61B 3/10* (2006.01)
*A61B 3/00* (2006.01)

(52) U.S. Cl.
USPC .................... 351/206; 351/211; 351/246

(58) Field of Classification Search
USPC ............................................. 351/200–246
See application file for complete search history.

(56) References Cited

U.S. PATENT DOCUMENTS

| 7,029,120 | B2 | 4/2006 | Kushida |
| 7,210,781 | B2 | 5/2007 | Kushida |
| 7,364,295 | B2 | 4/2008 | Tawada |
| 7,470,025 | B2 | 12/2008 | Iwanaga |
| 7,566,132 | B2 | 7/2009 | Fukuma et al. |
| 7,695,139 | B2 | 4/2010 | Ishikura |
| 8,235,528 | B2 * | 8/2012 | Mukai et al. ............ 351/208 |
| 8,308,297 | B2 | 11/2012 | Hirose et al. |
| 8,390,818 | B2 | 3/2013 | Hirose et al. |
| 8,482,859 | B2 * | 7/2013 | Border et al. ............ 359/630 |
| 8,556,424 | B2 * | 10/2013 | Iwase et al. ............ 351/206 |
| 2003/0234908 | A1 | 12/2003 | Kushida |
| 2006/0082728 | A1 | 4/2006 | Kushida |
| 2006/0114412 | A1 | 6/2006 | Tawada |
| 2006/0132711 | A1 | 6/2006 | Iwanaga |

(Continued)

FOREIGN PATENT DOCUMENTS

| CN | 1468582 A | 1/2004 |
| CN | 1810202 A | 8/2006 |

(Continued)

OTHER PUBLICATIONS

Jun. 7, 2013 European Search Report in European Patent Appln. No. 13000666.1.

(Continued)

*Primary Examiner* — Mohammed Hasan
(74) *Attorney, Agent, or Firm* — Fitzpatrick, Cella, Harper & Scinto (57) ABSTRACT

Provided is an imaging apparatus for photographing an image by an intensity of return light obtained from an eye to be inspected irradiated with measuring light, the imaging apparatus including: a fixation target for the eye to be inspected to fixate, an illuminated position setting unit for setting an illuminated position of the fixation target; and an illuminated position controlling unit for controlling the illuminated position setting unit so as to move the illuminated position of the fixation target for a first observation area to an illuminated position of the fixation target for a second observation area, in which the imaging apparatus calculates a movement distance of the illuminated position of the fixation target on the basis of a diopter scale of the eye to be inspected.

19 Claims, 5 Drawing Sheets

(56) References Cited

U.S. PATENT DOCUMENTS

| | | |
|---|---|---|
| 2007/0146636 A1 | 6/2007 | Ishikura |
| 2007/0236660 A1 | 10/2007 | Fukuma et al. |
| 2009/0091766 A1 | 4/2009 | Hirose |
| 2009/0285354 A1 | 11/2009 | Hirose et al. |
| 2010/0014052 A1 | 1/2010 | Koschmieder et al. |
| 2010/0277692 A1 | 11/2010 | Mukai et al. |
| 2011/0234975 A1 | 9/2011 | Hirose |
| 2011/0273668 A1 | 11/2011 | Hirose |
| 2011/0301455 A1 | 12/2011 | Numajiri et al. |
| 2012/0044455 A1 | 2/2012 | Hirose |
| 2012/0293770 A1 | 11/2012 | Hirose |
| 2012/0320338 A1 | 12/2012 | Hirose et al. |

FOREIGN PATENT DOCUMENTS

| | | |
|---|---|---|
| CN | 1989894 A | 7/2007 |
| CN | 202113055 U | 1/2012 |
| JP | 10-174676 A | 6/1998 |
| JP | 2007-275374 A | 10/2007 |
| JP | 2010-259543 A | 11/2010 |
| WO | 2011007657 A1 | 1/2011 |

OTHER PUBLICATIONS

Jul. 31, 2014 European Official Action in European Patent Appln. No. 13000666.1.

Aug. 5, 2014 Chinese Official Action in Chinese Patent Appln. No. 201310055518.0.

* cited by examiner

IMAGING APPARATUS

BACKGROUND OF THE INVENTION

1. Field of the Invention

The present invention relates to an imaging apparatus, and more particularly, to an optical image photographing apparatus that is used for ophthalmological diagnosis and treatment or the like.

2. Description of the Related Art

A scanning laser ophthalmoscope (SLO) which uses a principle of a confocal laser microscope is an ophthalmological apparatus that performs a raster scanning on a fundus of the eye with laser light which is measurement light and obtains a planar image of the fundus of the eye based on the intensity of return light with a high resolution at a high speed.

Such an apparatus for photographing a planar image is hereinafter referred to as SLO apparatus.

In recent years, it has become possible to acquire a planar image of a retina with improved lateral resolution by increasing a beam diameter of measuring light in the SLO apparatus. However, along with the increase in the beam diameter of measuring light, there occurs a problem of decreases in an SN ratio and the resolution of a planar image of a retina due to aberration of an eye to be inspected when the planar image is acquired.

In order to solve the problem, there is developed an adaptive optics SLO apparatus including an adaptive optics system, in which aberration of an eye to be inspected is measured by a wavefront sensor in real time, and aberrations of measuring light and return light thereof generated in the eye to be inspected are corrected by a wavefront correction device. Thus, it is possible to acquire a planar image with high lateral resolution.

When a planar image with high lateral resolution is acquired, because of problems of optical aberrations of the apparatus itself and a longer photographing time, a photographing range of a single photography becomes small. As a result, there is a tendency that it becomes difficult to distinguish which part of the fundus the planar image corresponds to. In the invention disclosed in Japanese Patent Application Laid-Open No. 2010-259543, there is proposed a complex apparatus in which an SLO apparatus having a large field angle and an SLO apparatus having a small field angle with high resolution are combined so as to solve the problem.

In order to photograph a desired position of the eye to be inspected, a fixation target for fixating the eye to be inspected is often used. In the invention disclosed in Japanese Patent Application Laid-Open No. 2007-275374, a desired position in the fundus image is specified so as to change a projected position of the fixation target, and hence a fundus image of the desired position is easily acquired.

Here, if the eye to be inspected has ametropia, such as near sightedness or far sightedness, it is necessary to perform focus adjustment so that the subject can clearly see a display of the fixation target or that the acquired planar image can be clearly displayed. In this case, in some configurations of the optical system, a relationship between a display position of the fixation target and an amount of urging the eye to be inspected to rotate depends on a diopter scale of the eye to be inspected. Therefore, it is difficult to acquire a planar image of a desired position of the fundus.

SUMMARY OF THE INVENTION

In view of the above-mentioned problem, the present invention is to provide an imaging apparatus, which adjusts a display position of a fixation target in accordance with a diopter scale of an eye to be inspected, and hence a planar image of a desired position in a fundus can be easily acquired.

In order to achieve the above-mentioned object, according to an exemplary embodiment of the present invention, there is provided an imaging apparatus for photographing an eye to be inspected on the basis of return light from the eye to be inspected irradiated with measuring light, the imaging apparatus including; an imaging unit for photographing an area of the eye to be inspected corresponding to a first area of an image of the eye to be inspected by lighting a fixation target at a first position, and a changing unit for changing, in a case where an area of the eye to be inspected corresponding to a second area of the image of the eye to be inspected is photographed by the imaging unit, the first position to a second position at which the fixation target is lighted, on the basis of a distance between the first area and the second area and a diopter scale of the eye to be inspected.

Further, in order to deal with the above-mentioned matter, according to another exemplary embodiment of the present invention, there is provided a method of controlling an imaging apparatus for photographing an eye to be inspected on the basis of return light from the eye to be inspected irradiated with measuring light, the method including the steps of; photographing an area of the eye to be inspected corresponding to a first area of an image of the eye to be inspected by lighting a fixation target at a first position, and changing, in a case where an area of the eye to be inspected corresponding to the second area in the image of the eye to be inspected is photographed, the first position to a second position at which the fixation target is lighted, on the basis of a distance between the first area and the second area and a diopter scale of the eye to be inspected.

In view of the above-mentioned problem, the exemplary embodiment of the present invention can realize the imaging apparatus, which adjusts the display position of the fixation target according to the diopter scale of the eye to be inspected, and hence the planar image of a desired position in the fundus can be easily acquired.

Further features of the present invention will become apparent from the following description of exemplary embodiments with reference to the attached drawing.

DESCRIPTION OF THE EMBODIMENTS

Now, an embodiment of the present invention is described.

In this embodiment, an adaptive optics scanning laser ophthalmoscope (AOSLO) apparatus to which the present invention is applied is described as an optical image photographing apparatus. The AOSLO apparatus includes an adaptive optics system, and is an apparatus for photographing a planar image (AOSLO image) of a retina having high lateral resolution. In addition, for the purpose of aiding acquisition of the AOSLO image, a wide field scanning laser ophthalmoscope (WF-SLO), apparatus is associated, which performs photographing of a planar image having a wide field angle (WFSLO image).

In this embodiment, the AOSLO apparatus is configured to acquire a planar image by correcting optical aberration of an eye to be inspected by using a spatial light modulator, and hence a good planar image can be acquired regardless of a diopter scale and optical aberration of the eye to be inspected.

Here, in order to photograph a planar image having high lateral resolution, the apparatus includes the adaptive optics system. However, the adaptive optics system may not be included as long as the configuration of the optical system can realize high resolution.

(Whole Apparatus)

Figure 1A:
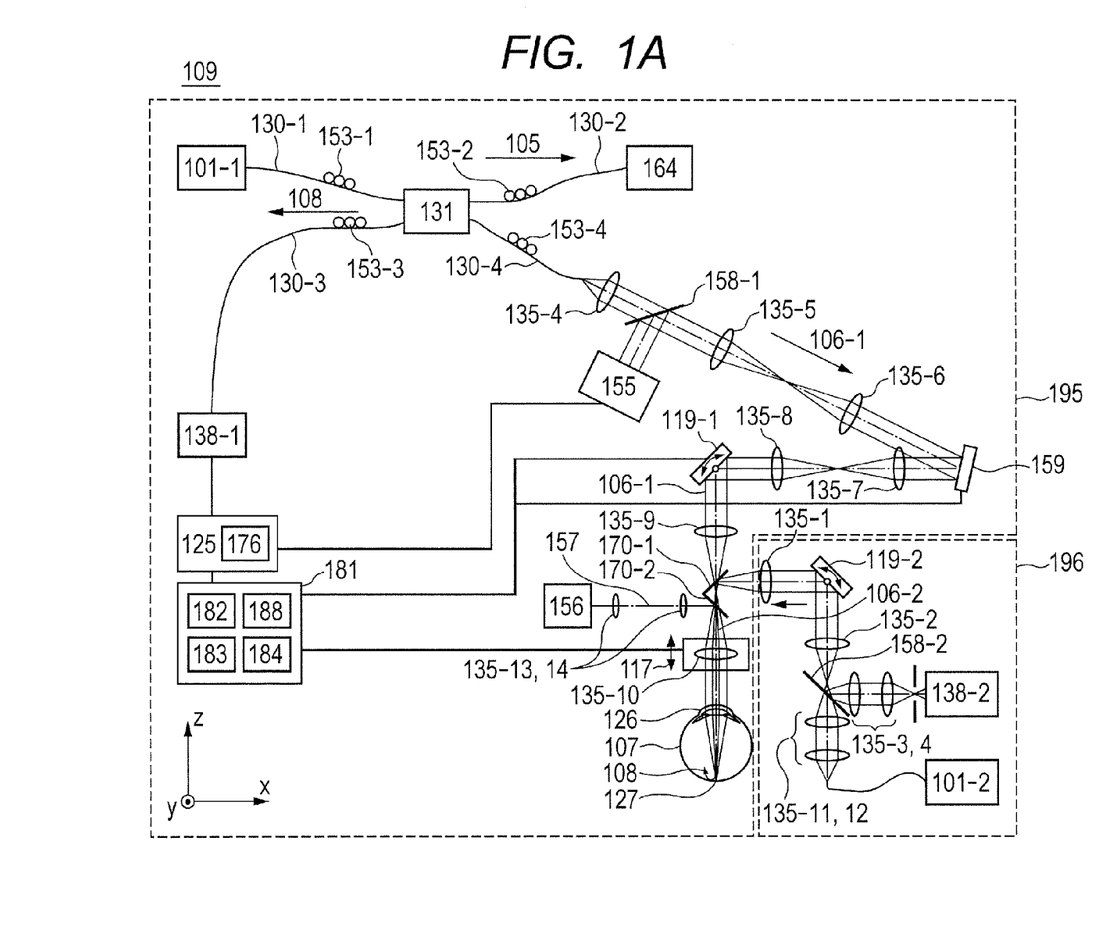
FIG. 1A is a diagram illustrating a general configuration of an SLO apparatus according to an embodiment of the present invention.

First, a schematic configuration of an AOSLO apparatus 109 according to this embodiment is described specifically with reference to FIG. 1A. The AOSLO apparatus 109 roughly includes an AOSLO portion 195 for acquiring the AOSLO image and a WFSLO portion 196 for acquiring a wide field SLO image (WFSLO image).

(Whole AOSLO Portion)

First, a whole AOSLO portion is described.

Light emitted from a light source 101-1 is split by an optical coupler 131 into reference light 105 and measuring light 106-1. The measuring light 106-1 is guided to an eye to be inspected 107 as an observation target through a single mode fiber 130-4, a spatial light modulator 159, an XY scanner 119-1, a dichroic mirror 170-2, and the like. The AOSLO portion also includes a fixation target 156, and a light flux 157 from the fixation target 156 has a role of urging the eye to be inspected 107 to fixate or rotate.

The measuring light 106-1 becomes return light 108 after being reflected or scattered by the eye to be inspected 107, and the return light 108 propagates in the opposite direction in the optical path and enters a detector 138-1 through the optical coupler 131. The detector 138-1 converts optical intensity of the return light 108 into a voltage signal, which is used for forming a planar image of the eye to be inspected 107. In this embodiment, the whole optical system is mainly constituted of a refracting optical system using lenses. However, it is possible to constitute the optical system by using a reflecting optical system using spherical mirrors instead of the lenses.

In addition, a reflection type spatial light modulator is used as an aberration correction device in this embodiment, but it is possible to use a transparent type spatial light modulator or a variable shape mirror.

The AOSLO portion described above works as a photographing portion, which photographs an image of the eye to be inspected by first return light from the eye to be inspected of using first measuring light projected to the eye to be inspected from the light source. In addition, the AOSLO portion works as a second photographing portion as necessary, which photographs a second image of the eye to be inspected by using second return light of second measuring light projected to the eye to be inspected.

(Light Source of AOSLO)

Next, details of the light source 101-1 are described. The light source 101-1 is a super luminescent diode (SLD) serving as a typical low-coherent light source. A wavelength of the light source 101-1 is 830 nm and a bandwidth thereof is 50 nm. Here, in order to acquire a planar image having little speckle noise, a low-coherent light source is selected. Further, although the SLD is selected as the light source, any type of light source may be used as long as the light source can emit low-coherent light. For example, an amplified spontaneous emission (ASE) light source may be used.

In view of the measurement of the eye, a suitable wavelength is a near infrared light wavelength. The wavelength affects the resolution of the acquired planar image in a lateral direction, and hence a minimum wavelength is desired. Therefore, in this embodiment, the wavelength is set to 830 nm. Another wavelength may be selected depending on a measurement area of the observation object.

The light emitted from the light source 101-1 is guided to the optical coupler 131 through a single mode fiber 130-1 and split into the reference light 105 and the measuring light 106-1 in a ratio of 96:4. Polarization controllers 153-1 to 153-4 are provided on the respective signal mode fibers.

(Reference Optical Path of AOSLO)

Next, an optical path of the reference light 105 is described.

The reference light 105 split by the optical coupler 131 enters a light intensity measuring apparatus 164 through an optical fiber 130-2. The light intensity measuring apparatus 164 is used for measuring light intensity of the reference light 105 so as to monitor the light intensity of the measuring light 106-1.

(Measuring Optical Path of AOSLO)

Next, an optical path of measuring light 106 is described.

The measuring light 106-1 split by the optical coupler 131 is led to a lens 135-4 through the single mode fiber 130-4, and is adjusted to be a collimated beam having a beam diameter of 4 mm. The measuring light 106-1 passes through a beam splitter 158-1 and lenses 135-5 to 135-6, and enters the spatial light modulator 159.

Here, the spatial light modulator 159 is controlled by a personal computer 125 via a spatial light modulator driver 188 in a driver portion 181.

Next, the measuring light 106-1 is modulated by the spatial light modulator 159, passes through lenses 135-7 to 135-8, and enters a mirror of the XY scanner 119-1. For simplification, the XY scanner 119-1 is illustrated as a single mirror. However, in an actual case, two mirrors, that is, an X scanner and a Y scanner, are disposed close to each other to raster-scan a retina 127 in a direction perpendicular to the optical axis. The center of the measuring light 106 is adjusted to align with the center of rotation of the mirrors of the XY scanner 119-1.

Here, the X scanner is a scanner for scanning the measuring light 106 in a direction parallel to the paper plane, and a resonance type scanner is used for the X scanner here. The drive frequency is approximately 7.9 kHz. In addition, the Y scanner is a scanner for scanning the measuring light 106 in a direction perpendicular to the paper plane, and a galvano scanner is used for the Y scanner here. The drive waveform is a saw tooth wave, the frequency is 64 Hz, and the duty ratio is 16%. The drive frequency of the Y scanner is an important parameter for determining a frame rate of the AOSLO image photography.

Here, the XY scanner 119-1 is controlled by the personal computer 125 through an optical scanner driver 182 included in the driver portion 181. Spherical lenses (mirrors) 135-9 and 135-10 correspond to an optical system for scanning the retina 127 and serve to scan the retina 127 with the measuring light 106 about the vicinity of a cornea 126.

Here, the beam diameter of the measuring light 106 is 4 mm, but the beam diameter may be larger than 4 mm in order to acquire an optical image with higher resolution. An electric stage 117 may be moved in a direction indicated by the arrows to adjust and control the position of the associated spherical lens 135-10.

Here, the electric stage 117 is controlled by the personal computer 125 through the electric stage driver 183 included in the driver portion 181.

The position of the lens 135-10 may be adjusted, to thereby condense the measuring light 106 to a predetermined layer of the retina 127 of the eye to be inspected 107 to observe the layer. In other words, the electric stage 117 works as a focusing unit in the present invention for permitting the measuring light to focus on the eye to be inspected, and the driver portion 181 and the electric stage driver 183 work as a focus control unit for controlling the focusing unit in accordance with an in-focus state of the measuring light. Note that, the personal computer 125 may work as an in-focus state acquiring unit for acquiring a position of the focusing unit in the optical path as the in-focus state. In addition, like this embodiment, it is necessary to consider an influence of the diopter scale in the case illustrated in FIG. 1A, in which the focus lens is disposed between the fixation target and the eye to be inspected. In this case, when the focus lens is moved for correcting the diopter scale of the eye to be inspected, the position where the fixation target is presented to the eye to be inspected is different depending on the diopter scale of the eye to be inspected.

The measuring light 106 enters the eye to be inspected 107 and is reflected or scattered by the retina 127 so as to be the return light 108, which is guided to the optical coupler 131 again, and reaches the detector 138-1 through a single mode fiber 130-3. As the detector 138-1, for example, an avalanche photo diode (APD) or a photomultiplier tube (PMT) is used, which is a high speed sensor with high sensitivity. The return light 108 is modulated again by the spatial light modulator 159.

In addition, a part of the return light 108 split by the beam splitter 158-1 enters a wavefront sensor 155, and an aberration of the return light 108 generated in the eye to be inspected 107 is measured. The wavefront sensor 155 is electrically connected to the personal computer 125. Here, the lenses 135-5 to 135-10 and the like are disposed so that the cornea 126, the XY scanner 119-1, the wavefront sensor 155, and the spatial light modulator 159 are optically conjugate to each other.

Here, the wavefront sensor 155 can measure an aberration of the eye to be inspected 107, and the wavefront sensor 155 is an element that can detect low order aberrations such as the diopter scale and high order aberrations such as wavefront aberration of the eye to be inspected. Example of the wavefront sensor 155 include a Shack-Hartmann wavefront sensor and a wavefront curvature sensor for detecting a variation in optical intensity. In addition, the spatial light modulator 159 can correct an aberration of the eye to be inspected 107. The wavefront sensor 155 and the spatial light modulator 159 respectively work as an aberration measuring unit in the present invention for measuring an aberration of the eye to be inspected and an aberration correcting unit in the present invention for correcting aberrations of the measuring light and the return light, or aberrations of the above-mentioned second measuring light and second return light, on the basis of the measured aberration in the present invention.

Further, on the basis of the obtained aberration as a measurement result of the wavefront sensor, the spatial light modulator 159 is controlled in real time so that the aberration generated in the eye to be inspected 107 is corrected, and hence a planar image with higher lateral resolution can be acquired.

Figure 1B:
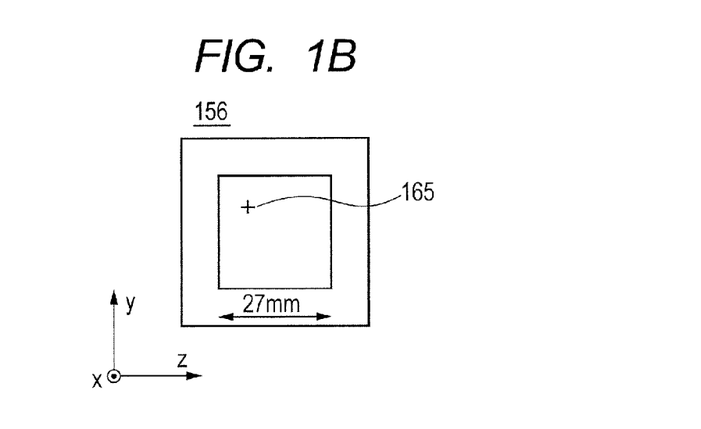
FIG. 1B is a diagram illustrating an example of a display screen of a fixation target in the SLO apparatus illustrated in FIG. 1A.
Figure 1C:
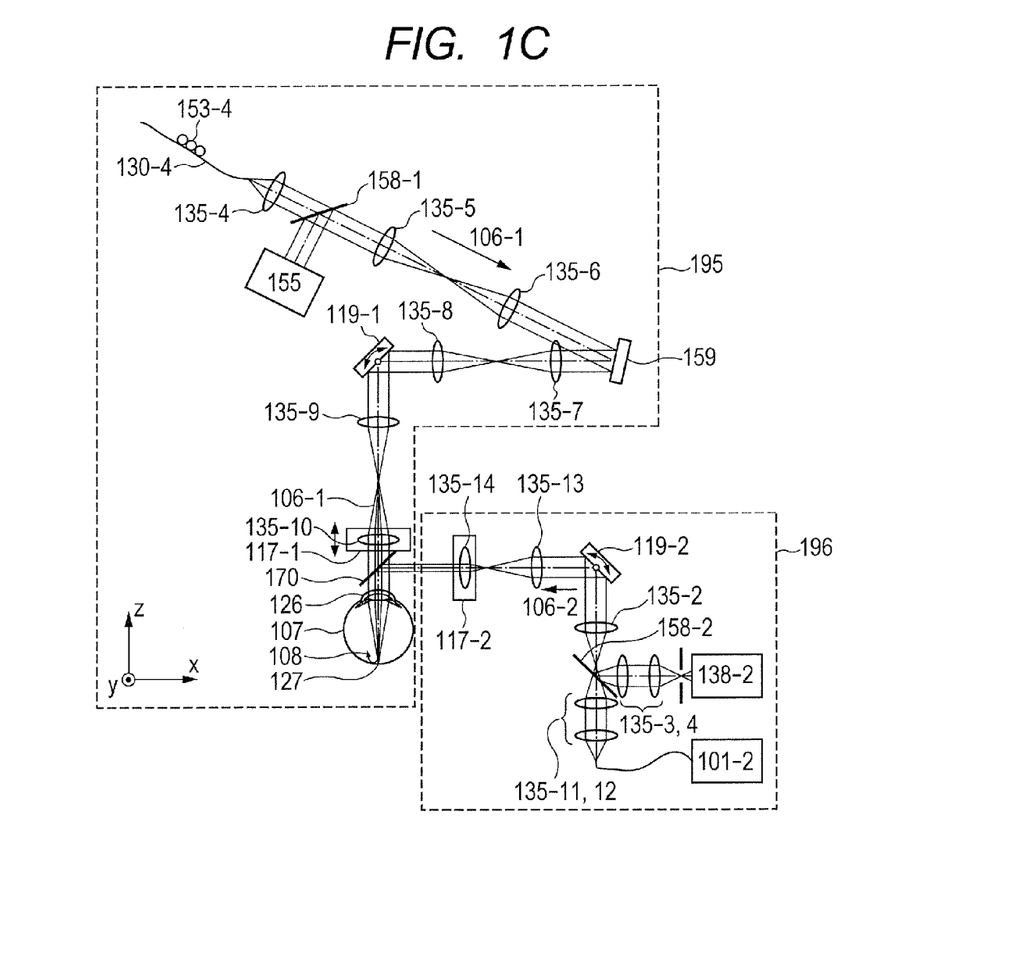
FIG. 1C is a diagram illustrating a modified example of the SLO apparatus according to the embodiment of the present invention.

In this embodiment, the lens 135-10 is a spherical lens, but a cylindrical lens may be used instead of the spherical lens 135-10 depending on an aberration (refractive error) of the eye to be inspected 107. An additional lens may be provided on the optical path of the measuring light 106. Here, the lens 135-10 and the electric stage 117 are shared by the AOSLO portion 195 and the WFSLO portion 196. However, it is possible to dispose the lens and the electric stage independently of each other as illustrated in FIG. 1C. In this case, the electric stages of the AOSLO portion 195 and the WFSLO portion 196 may be operated in synchronization with each other.

In this embodiment, the measuring light 106 is used for measuring the aberration with the wavefront sensor 155. However, it is possible to use other light source for measuring the aberration. In addition, it is possible to form other optical path for measuring the aberration.

For instance, it is possible to use a beam splitter so that the light for measuring the aberration enters from between the spherical lens 135-10 and the cornea 126.

The fixation target 156 includes a light-emitting type display module and has a display surface (27 mm square, 128× 128 pixels) on a YZ-plane. In this embodiment, any one of a liquid crystal array, an organic EL array, and an LED array may be used. The eye to be inspected 107 gazes the light flux 157 from the fixation target 156 to urge the fixation or rotation of the eye to be inspected 107. For example, as illustrated in FIG. 1B, a cross pattern is blinked on the display surface of the fixation target 156 at an arbitrary illuminated position 165.

The light flux 157 from the fixation target 156 is guided to the retina 127 through lenses 135-13 and 135-14, the dichroic mirror 170-2, and the lens 135-10. The fixation target 156 is used for urging the eye to be inspected to gaze the fixation target 156. The lenses 135-10, 135-13, and 135-14 are disposed so that the display surface of the fixation target 156 is optically conjugate with the retina 127. The fixation target 156 is controlled by the personal computer 125 through a fixation target driver 184 included in the driver portion 181. The fixation target driver 184 works as an illuminated position moving unit for the fixation target for arbitrarily moving an illuminated position of the fixation target.

(Measurement System of AOSLO)

Next, a configuration of the measurement system is described.

The SLO apparatus 109 can acquire the planar image (SLO image) constituted of intensities of the return light 108 from the retina 127.

The return light 108 as light reflected or scattered by the retina 127 enters the detector 138-1 through the lenses 135-4 to 135-10, the spatial light modulator 159, the optical coupler 131, and the like, and the light intensity is converted into a voltage signal.

The voltage signal obtained by the detector 138-1 is converted into a digital value by an AD board 176 in the personal computer 125. The personal computer 125 performs data processing in synchronization with operation of the XY scanner 119-1 and the drive frequency so as to form the planar image. Here, the fetch speed of the AD board 176 is 15 MHz.

In addition, a part of the return light 108 split by the beam splitter 158-1 enters the wavefront sensor 155, and hence an aberration of the return light 108 is measured. The wavefront sensor 155 is a Shack-Hartmann wavefront sensor having a measuring range as narrow as −1D to +1D and high measuring accuracy.

The obtained aberration is expressed by using a Zernike polynomial, which indicates an aberration of the eye to be inspected 107.

The Zernike polynomial includes a tilt (inclination) term, a defocus term, an astigmatism term, a coma term, and a trefoil term.

(Method of Acquiring AOSLO Image)

Next, a method of acquiring the planar image (AOSLO image) is described with reference to FIGS. 2A to 2D.

Figure 2A:
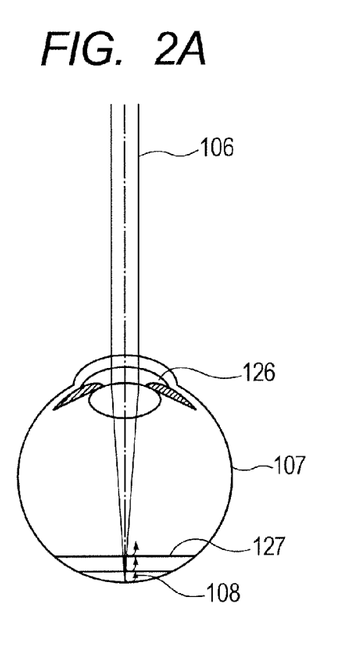
FIG. 2A is a diagram illustrating a method of acquiring an image by the SLO apparatus according to the embodiment of the present invention.

The SLO apparatus 109 controls the XY scanner 119-1 and acquires intensities of the return light 108 with the detector 138-1 so as to acquire the planar image of the retina 127. Now, a method of acquiring the planar image of the retina 127 (in the plane perpendicular to the optical axis) is described.

FIG. 2A is a schematic diagram of the eye to be inspected 107 and illustrates a manner in which the eye to be inspected 107 is observed by the SLO apparatus 109.

As illustrated in FIG. 2A, the measuring light 106 enters the retina 127 through the cornea 126 and is reflected or scattered at various positions to be the return light 108, which reaches the detector 138-1.

Figure 2B:
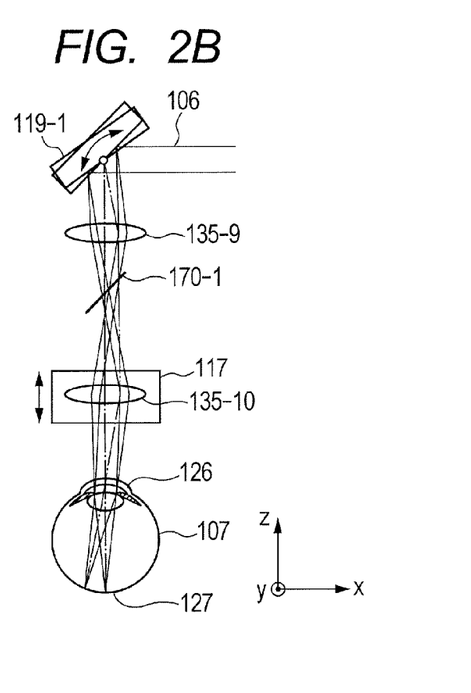
FIG. 2B is a diagram schematically illustrating a method of scanning the fundus of an eye to be inspected.

Further, as illustrated in FIG. 2B, the XY scanner 119-1 is driven in an X direction while detecting intensities of the return light 108, and hence information at individual positions in an X axis can be acquired.

Figure 2C:
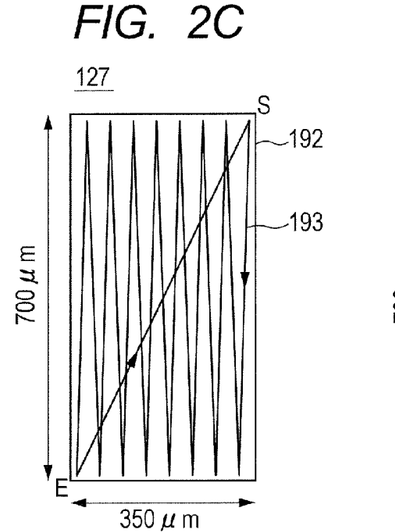
FIG. 2C is a diagram illustrating details of raster scan performed in the embodiment of the present invention.

Further, as illustrated in FIG. 2C, the XY scanner 119-1 is driven simultaneously in the X axis direction and in the Y axis direction, and hence raster scan of the retina 127 in a photographing range 192 is performed with the measuring light 106 as indicated by a locus 193 so as to detect intensities of the return light 108. Thus, as illustrated as a planar image 177 (in FIG. 2D), two-dimensional distribution of intensities of the return light 108 is obtained.

Here, the measuring light 106 is scanned from an upper right point S to a lower left point E, and intensities of the return light 108 during the scanning are used for constituting the planar image 177. The locus 193 from the point E to the point S is preparation for the next photography of the planar image 177. The ratio of time period necessary for the scan is 84% for the point S to the point E and 16% for the point E to the point S in the locus 193 illustrated in FIG. 2C, and this ratio is based on the duty ratio of the above-mentioned drive waveform of the Y scanner. In addition, for simple illustration, FIG. 2C illustrates the number of times of scanning in the X direction of the locus 193 to be smaller than in reality.

Figure 2D:
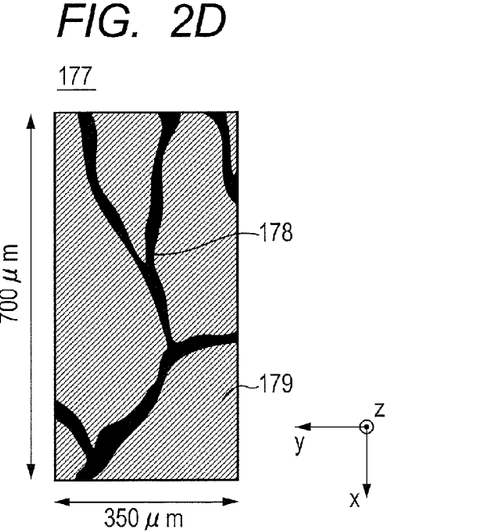
FIG. 2D is a diagram illustrating an example of a planar image acquired by the scan.

Here, the planar image 177 has a size of 700×350 μm, and a time period necessary for acquiring the planar image 177 is approximately 15.6 ms. The time period is based on the drive frequency of the Y scanner.

In addition, in the planar image 177, photoreceptor cells 179 having a relatively large intensity of the return light 108 are displayed brightly, while blood vessels 178 having a relatively small intensity are displayed darkly. In addition, blood corpuscles (not shown) in the blood vessel 178 are displayed brightly.

(Whole WFSLO Portion)

Next, a whole WFSLO portion is described. The WFSLO portion basically has the same configuration as that of the AOSLO portion except that the WFSLO portion does not include the adaptive optics system and the reference optical path. Overlapping description of the same part is omitted.

Light emitted from a light source 101-2 is guided to the eye to be inspected 107 as the observation target through lenses 135, an XY scanner 119-2, a dichroic mirror 170-1, and the like.

(Light Source of WFSLO)

Next, details of the light source 101-2 are described. As with AAOSLO, the light source 101-2 is an SLD. A wavelength of the light source 110-2 is 910 nm and a bandwidth thereof is 10 nm. Here, in order to separate the optical path of the AOSLO from the optical path of the WFSLO by using the dichroic mirror, the individual light sources have different wavelengths.

(Measuring Optical Path of WFSLO)

Next, an optical path of measuring light 106-2 is described.

The measuring light 106-2 emitted from the light source 101-2 is guided to the eye to be inspected 107 as the observation target through the lenses 135, the XY scanner 119-2, the dichroic mirror 170-1, and the like.

Here, the X scanner, which is the component of the XY scanner 119-2, is a scanner for scanning the measuring light 106-2 in a direction parallel to the paper plane, and a resonance type scanner is used for the X scanner here. The drive frequency is approximately 3.9 kHz. In addition, the Y scanner is a scanner for scanning the measuring light 106-2 in a direction perpendicular to the paper plane, and a galvano scanner is used for the Y scanner here. The drive waveform is a saw tooth wave, the frequency is 15 Hz, and the duty ratio is 16%. The drive frequency of the Y scanner is an important parameter for determining a frame rate of the WFSLO image photography.

Here, the beam diameter of the measuring light 106-2 is 1 mm, but the beam diameter may be larger than 1 mm in order to acquire an optical image with higher resolution.

The measuring light 106-2 enters the eye to be inspected 107 and is reflected or scattered by the retina 127 so as to be return light 108-2, which reaches a detector 138-2 through the dichroic mirror 170-1, the lens 135-1, the XY scanner 119-2, a beam splitter 158-2, and the like.

(Method of Acquiring WFSLO Image)

Next, a method of acquiring a wild field planar image (WFSLO image) is described.

The SLO apparatus 109 controls the XY scanner 119-2 and acquires intensities of the return light 108 with the detector 138-2 so as to acquire the wide field planar image of the retina 127. The method of acquiring the wide field planar image of the retina 127 (in the plane perpendicular to the optical axis) is the same as the method of acquiring the AOSLO image, and hence description thereof is therefore omitted.

(AOSLO Image Acquiring Procedure)

Next, a method of acquiring the planar image by using the SLO apparatus as a feature of the present invention is described. The SLO apparatus 109 uses the WFSLO portion 196 so as to permit the measuring light 106-2 to focus on the retina 127 for photographing the WFSLO image. Further, the diopter scale of the eye to be inspected is calculated based on a position of the electric stage 117 in the in-focus state. This operation is performed by a module region in the personal computer 125, which works as a diopter acquiring unit for acquiring the diopter scale of the eye to be inspected based on the in-focus state acquired by the focus control unit. For instance, it is possible to acquire, as diopter scale of the eye to be inspected, a position to which the focus lens is moved so that a contrast of the fundus image of the eye to be inspected photographed as the WFSLO image or the like becomes a designated contrast. Note that, the diopter acquiring unit may determine the diopter scale by calculation using a position of the focus lens in the optical axis direction, for example, or may acquire the diopter scale by using a table in which the position of the focus lens and the diopter scale are associated with each other. As a matter of course, it is possible to acquire the diopter scale by using low order aberrations detected by the wavefront sensor 155.

Next, a position at which the AOSLO image should be acquired in the WFSLO image is designated, and the display position of the fixation target 156 is calculated on the basis of the acquired diopter scale of the eye to be inspected and is displayed. Thus, the AOSLO image at a desired position can be acquired. In other words, the fixation target 156 is lighted at a first position, and in this state, the WFSLO portion 196 acquires the image of the eye to be inspected as the WFSLO image. The AOSLO portion as an imaging unit images or photographs an area of the real eye to be inspected corresponding to the area photographed as a first area in the WFSLO image. Further, when photographing an area of the real eye to be inspected corresponding to the area photographed as a second area in the acquired WFSLO image, the position at which the fixation target 156 is lighted is changed from the first position to the second position on the basis of a distance between the first area and the second area and the diopter scale of the eye to be inspected. This change of the illuminated position of the fixation target 156 is performed by a module region that works as a changing unit for performing the changing operation in the configuration exemplified as the personal computer 125 controlling the apparatus. Note that, in this embodiment, the diopter scale of the eye to be inspected is obtained by measurement in the real in-focus state. However, it is possible to dispose a diopter acquiring unit for acquiring the diopter scale of the eye to be inspected from an external device such as other ophthalmological apparatus or an external memory, and to calculate the display position of the fixation target 156 on the basis of the acquired diopter scale. For instance, it is possible to acquire the diopter scale of the eye to be inspected, which is externally acquired as a result of measurement using a fundus ring image of the eye to be inspected by a refractometer (eye refractive power measuring apparatus) or the like. Now, a unit for acquiring the planar image of the retina 127 of the eye to be inspected 107 having a diopter scale of −5D is described. In particular, observation of the papilla of the eye to be inspected 107 is aimed at.

Figure 3:
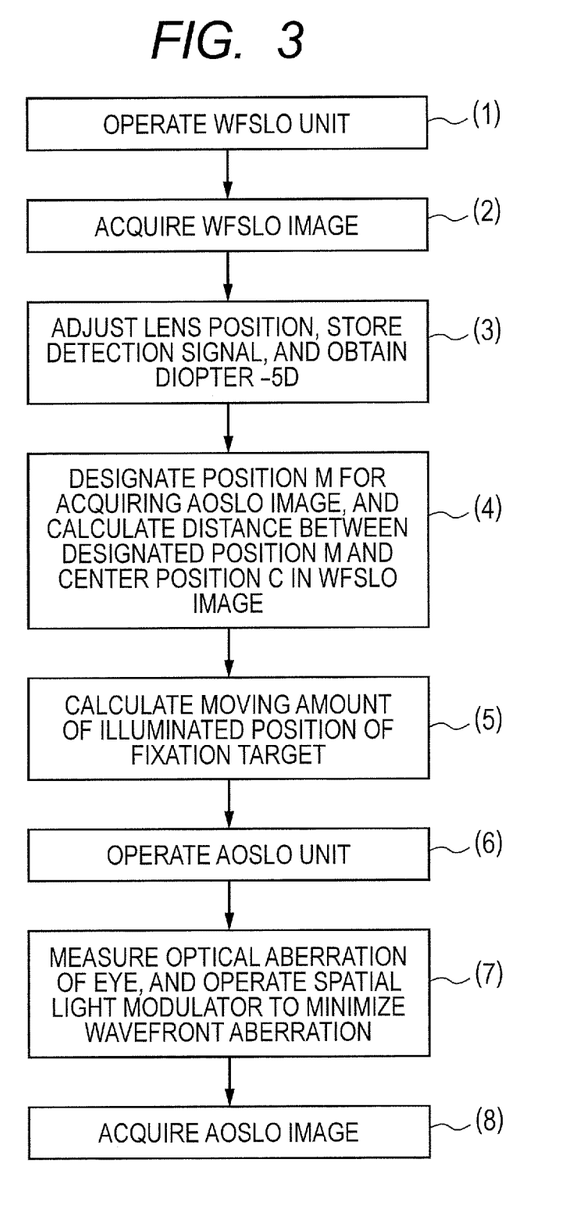
FIG. 3 is a flowchart illustrating a procedure of acquiring an image by the SLO apparatus according to the embodiment of the present invention.

In the method of acquiring the planar image, the following steps (1) to (8) are performed successively, for example. Otherwise, it is possible to return to a former step as necessary. In addition, it is possible to use a computer or the like so as to automatically perform the following steps. FIG. 3 is a flowchart illustrating the method of acquiring the planar image.

(1) Perform operation of the WFSLO portion 196. The measuring light 106-2 enters the eye to be inspected 107. Here, the position of the lens 135-10 is adjusted so that the measuring light 106-2 enters the eye to be inspected 107 in a state of being collimated light. In addition, a cross pattern of the fixation target 156 is lighted in the center of the display screen, and the eye to be inspected is urged to fixate the front.

(2) Drive the XY scanner 119-2 while acquiring the signal of the detector 138-2 so that the WFSLO image is acquired. These steps correspond to a first step of urging the eye to be inspected to fixate the illuminated position of the fixation target so as to acquire a first image by a first photographing portion. The WFSOL image corresponds to an image of a first observation area in the present invention.

(3) Perform the step (2) repeatedly, adjust a position of the lens 135-10 by using the electric stage 117 so that the WFSLO image becomes clear, and record the signal of the detector 138-2. This position of the lens 135-10 as the focusing unit in the optical path is acquired as an in-focus state or information related thereto by a module region in the personal computer 125, which works as an in-focus state detecting unit. The diopter acquiring unit for calculating the diopter scale acquires the diopter scale of the eye to be inspected on the basis of the in-focus state. In this case, in order to acquire an appropriate image by determining whether or not clarity of the WFSLO image is good, it is possible to use a contrast or signal intensity as an index of the image state and to determine whether or not clarity of the image to be used is good by evaluating the index in the focusing unit. In addition, in this case, it is preferred that the focusing unit can focus on a desired layer of the retina of the eye to be inspected with the measuring light or the second measuring light. Thus, it is possible to perform inspection of various layers.

Figure 4A:
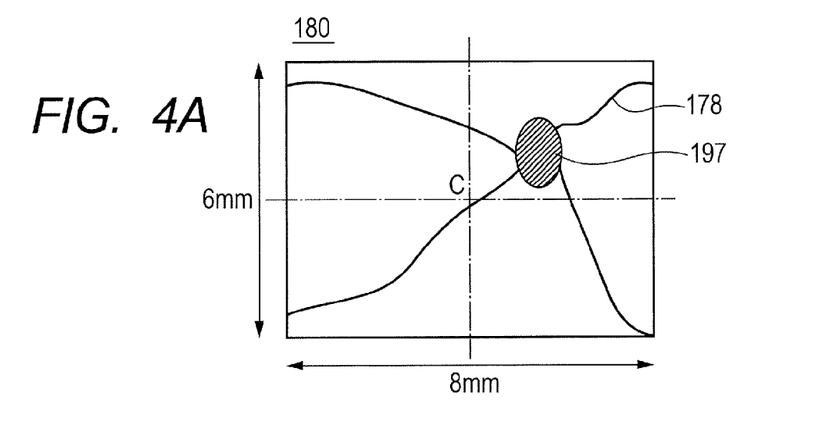
FIGS. 4A, 4B and 4C are diagrams illustrating a method of controlling a fixation target of the SLO apparatus according to the embodiment of the present invention, and are diagrams illustrating an example of WFSLO images acquired in the image acquiring procedure.

Here, subsequent steps are described with reference to the WFSLO image exemplified in FIGS. 4A to 4C. FIG. 4A is a schematic diagram of a WFSLO image 180. Here, a size of the WFSLO image is 6×8 mm. The blood vessels 178 and a papilla 197 can be observed. In addition, a diopter scale of the eye to be inspected 107 at −5D is obtained from the position of the electric stage 117. These steps correspond to a third step of the present invention, in which an adjustment state of the focusing unit is referred to so that the diopter scale of the eye to be inspected is calculated.

Figure 4B:
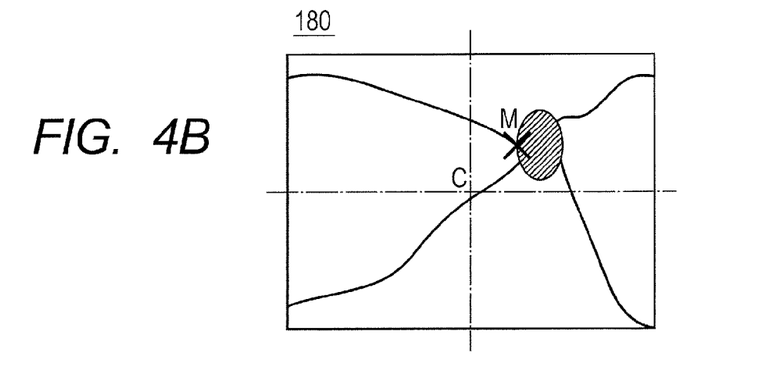
Figure 4C:
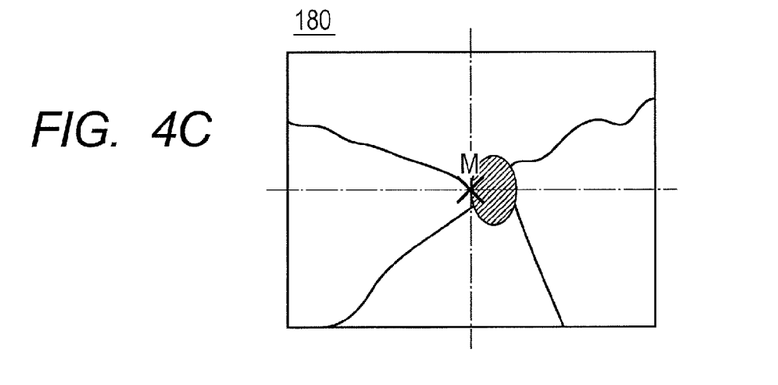

(4) Click with a mouse (not shown) a position M near an intersection between the papilla 197 and the blood vessel 178 illustrated in FIG. 4B of the WFSLO image 180 displayed on a monitor (not shown) of the personal computer 125 so as to designate an acquiring position of the AOSLO image as a second observation area in the present invention. Next, calculate a distance between the designated position M and a center position C of the WFSLO image 180. The distance between positions C and M was 1.80 mm. Here, the acquiring position of the AOSLO image is input by the mouse, but it is possible to input the position as coordinates. These steps correspond to a fourth step of the present invention, in which a desired position in the first image is designated, and an image distance that is a distance between the center of the first image and a desired position is calculated.

(5) Calculate a moving amount of the illuminated position of the fixation target 156. In addition, when a moving amount of the illuminated position of the fixation target is a distance between the first position and the second position, it is possible to say that the second position is acquired on the basis of the distance and the diopter scale of the eye to be inspected. This operation is performed by the diopter acquiring unit for acquiring the diopter scale of the eye to be inspected from the eye refractive power measuring apparatus and an illuminated position acquiring unit for acquiring the second position on the basis of the calculated movement distance and the acquired diopter scale. In this embodiment, if the diopter scale is 0D, 6 mm of the WFSLO image corresponds to 25.2 mm of the fixation target 156, and the distance between the positions C and M of 1.80 mm corresponds to 7.56 mm on the fixation target 156. Here, because the diopter scale of the eye to be inspected is −5D, the above-mentioned value 7.56 mm is converted into 8.01 mm by multiplying a conversion coefficient of 1.06 determined by designing the optical system. When the illuminated position of the fixation target 156 is moved by 8.01 mm so as to correspond to the direction from the position C to M, the position M of the papilla 197 can be moved to a position near the center of the WFSLO image by this operation as illustrated in FIG. 4C.

Here, the above-mentioned conversion coefficient is calculated for each diopter scale. For instance, the conversion coefficient is 0.96 for a diopter scale of +5D, 1.02 for 0D, 1.06 for −5D, and 1.12 for −10D.

These steps correspond to a fifth step of the present invention, in which a moving amount of the illuminated position of the fixation target is calculated on the basis of the image distance and the diopter scale of the eye to be inspected. In other words, when images of the first observation area and the second observation area in the eye to be inspected are photographed, the steps work as a movement distance calculating unit of the present invention, which calculates a movement distance of the illuminated position from an illuminated position of the fixation target when the first observation area is photographed to an illuminated position of the fixation target when the second observation area is photographed, on the basis of the diopter scale of the eye to be inspected. In addition, when the moving amount of the illuminated position of the fixation target is the distance between the first position and the second position, the steps work as an illuminated position acquiring unit for acquiring the second position on the basis of the distance and the diopter scale of the eye to be inspected. The steps are performed by a configuration exemplified as a module region in the personal computer 125. In addition, it is preferred that the movement distance calculating unit store the above-mentioned conversion coefficient as a conversion table for calculating the movement distance of the fixation target on the basis of the distance between the first observation area and the second observation area and the diopter scale of the eye to be inspected.

(6) Perform operation of the AOSLO portion 195. The measuring light 106-1 enters the eye to be inspected 107. This operation and the subsequent operations correspond to a sixth step of the present invention, in which the illuminated position of the fixation target is moved on the basis of the calculated moving amount of the illuminated position so as to urge the eye to be inspected to fixate the illuminated position after the movement, and a seventh step of the present invention, in which the second image is acquired by the second photographing portion.

(7) Measure a part of the return light 108 by the wavefront sensor 155 so as to acquire an optical aberration of the eye to be inspected 107. Control the spatial light modulator 159 to minimize the acquired wavefront aberration. Here, feedback control is performed by using the wavefront sensor 155, the spatial light modulator 159, and the personal computer 125 to minimize the wavefront. Thus, a surface shape of the spatial light modulator 159 is controlled in real time. In other words, in these steps, on the basis of the aberration measured by the aberration measuring unit for measuring the aberration of the eye to be inspected, the aberration correcting unit performs correction of aberrations of the second measuring light and the second return light. In addition, focusing on the eye to be inspected with the second measuring light in this case is also performed by the above-mentioned focusing unit in this embodiment. However, it is possible to perform the focusing by an independent focusing unit disposed for the second measuring light.

(8) Acquire the AOSLO image from the signal obtained by the detector 138-1 while driving the XY scanner 119-1. Here, because the eye to be inspected 107 is urged in the step (5) so that a position near the intersection between the papilla 197 and the blood vessel of the eye to be inspected 107 becomes the optical axis center, the AOSLO image whose center is near the position is acquired. Here, it is possible to adjust the position of the lens 135-10 by using the electric stage 117 so as to photograph other layer of the retina 127.

As described above, because the moving amount of the illuminated position of the fixation target is calculated by considering the diopter scale of the eye to be inspected, it is possible to correctly urge the eye to be inspected to rotate regardless of the diopter scale of the eye to be inspected. Therefore, it is possible to easily acquire the optical image of a desired position.

In addition, by calculating the diopter scale of the eye to be inspected through use of information on a position of the lens for adjusting the focus of the WFSLO portion, or by using the diopter scale acquired by other ophthalmological equipment, it is possible to easily acquire the optical image of a desired position by a simple configuration.

In addition, by calculating the moving amount of the illuminated position of the fixation target through use of the conversion table, it is possible to acquire the optical image of a desired position by a simple configuration.

In addition, by adjusting the focus through use of an image contrast or intensity of the WFSLO image as an index, it is possible to easily acquire the diopter scale of the eye to be inspected. In addition, it is possible to adjust the focus automatically by using a computer.

In addition, by disposing the AOSLO portion for measuring an aberration of the eye to be inspected so as to correct the aberration, it is possible to acquire the AOSLO image with high resolution.

By sharing the same lens for adjusting focus of the WFSLO portion and the AOSLO portion, it is possible to provide an apparatus having a simple configuration (claim 8).

It is possible to acquire the AOSLO image of a desired layer of the retina by adjusting the lens for performing adjustment of focus of the AOSLO portion so as to focus on the desired layer of the retina with the measuring light.

Note that, the above-mentioned configuration is an example of a configuration defined as a unit for performing various steps in the present invention, which can be substituted by various known configurations that can obtain the same function. The substitutable configurations are also included in the concept of the unit defined by the present invention.

Another Embodiment

Further, the present invention is also implemented by executing the following processing. Specifically, in this processing, software (program) for implementing the functions of the above-mentioned embodiment is supplied to a system or an apparatus via a network or various kinds of storage medium, and a computer (or CPU, MPU, etc.) of the system or the apparatus reads out and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent configurations and functions.

This application claims the benefit of Japanese Patent Application No. 2012-035089, filed Feb. 21, 2012, which is hereby incorporated by reference herein in its entirety.

What is claimed is:

1. An imaging apparatus for acquiring an image of an eye to be inspected on the basis of return light from the eye to be inspected irradiated with measuring light, the imaging apparatus comprising:

an imaging unit configured to acquire an image of an area of the eye to be inspected corresponding to a first area in an image of the eye to be inspected by lighting a fixation target at a first position; and a changing unit configured to change, in a case where an image of an area of the eye to be inspected corresponding to a second area in an image of the eye to be inspected is acquired by the imaging unit, the first position to a second position at which the fixation target is lighted, on the basis of a distance between the first area and the second area and a diopter scale of the eye to be inspected.

2. An imaging apparatus according to claim 1, further comprising:
a diopter acquiring unit configured to acquire the diopter scale of the eye to be inspected on the basis of an in-focus state of a focusing unit in a case where the fixation target is presented to the eye to be inspected through the focusing unit; and
a position acquiring unit configured to acquire the second position on the basis of the distance and the acquired diopter scale.

3. An imaging apparatus according to claim 2, further comprising an in-focus state acquiring unit configured to acquire a position of the focusing unit in an optical path as the in-focus state,
wherein the diopter acquiring unit acquires the diopter scale of the eye to be inspected on the basis of the acquired position of the focusing unit in the optical path as the in-focus state.

4. An imaging apparatus according to claim 1, further comprising:
a diopter acquiring unit configured to acquire the diopter scale of the eye to be inspected from an eye refractive power measuring apparatus; and
a position acquiring unit configured to acquire the second position on the basis of the distance and the acquired diopter scale.

5. An imaging apparatus according to claim 1, further comprising a determination unit configured to determine a state of the image according to an index,
wherein the index comprises one of a contrast and an intensity of the image.

6. An imaging apparatus according to claim 1, further comprising a photographing portion configured to photograph a second image of the eye to be inspected with second return light from the eye to be inspected of second measuring light instead of the measuring light.

7. An imaging apparatus according to claim 6, further comprising:
an aberration measuring unit configured to measure an aberration of the eye to be inspected; and
an aberration correcting unit configured to correct aberrations of the second measuring light and the second return light on the basis of the measured aberration.

8. An imaging apparatus according to claim 6, further comprising a focus unit configured to focus on the eye to be inspected with the second measuring light.

9. An imaging apparatus according to claim 6, further comprising a focusing unit configured to focus on a desired layer of a retina of the eye to be inspected with the second measuring light.

10. A method of controlling an imaging apparatus for acquiring an image of an eye to be inspected on the basis of return light from the eye to be inspected irradiated with measuring light, the method comprising:
acquiring an image of an area of the eye to be inspected corresponding to a first area in an image of the eye to be inspected by lighting a fixation target at a first position; and changing, in a case where an image of an area of the eye to be inspected corresponding to a second area in an image of the eye to be inspected is acquired, the first position to a second position at which the fixation target is lighted, on the basis of a distance between the first area and the second area and a diopter scale of the eye to be inspected.

11. A method of controlling an imaging apparatus according to claim 10, further comprising the steps of:
acquiring the diopter scale of the eye to be inspected on the basis of an in-focus state of a focusing unit in a case where the fixation target is presented to the eye to be inspected through the focusing unit; and
acquiring the second position on the basis of the distance and the acquired diopter scale.

12. A method of controlling an imaging apparatus according to claim 11, further comprising as step of acquiring a position of the focusing unit in an optical path as the in-focus state,
wherein the acquiring of diopter scale comprises acquiring the diopter scale of the eye to be inspected on the basis of the acquired position of the focusing unit in the optical path as the in-focus state.

13. A method of controlling an imaging apparatus according to claim 10, further comprising the steps of:
acquiring the diopter scale of the eye to be inspected from an eye refractive power measuring apparatus; and
acquiring the second position on the basis of the distance and the acquired diopter scale.

14. A recording medium having recorded thereon a program for causing a computer to perform the steps of the method of controlling an imaging apparatus according to claim 10.

15. An imaging apparatus for acquiring an image of an eye to be inspected on the basis of return light from the eye to be inspected irradiated with measuring light, the imaging apparatus comprising:
an imaging unit configured to acquire an image of an area of the eye to be inspected corresponding to a first area of in an image of the eye to be inspected by lighting a fixation target at a first position; and
a changing unit configured to change, in a case where an image of an area of the eye to be inspected corresponding to a second area in an image of the eye to be inspected is acquired by the imaging unit, the first position to a second position at which the fixation target is lighted, on the basis of a distance between the first area and the second area and a position of a focusing unit in an optical path when the fixation target is presented to the eye to be inspected through the focusing unit.

16. An imaging apparatus according to claim 15, further comprising:
a diopter acquiring unit configured to acquire the diopter scale of the eye to be inspected on the basis of an in-focus state of the focusing unit in a case where the fixation target is presented to the eye to be inspected through the focusing unit; and
a position acquiring unit configured to acquire the second position on the basis of the distance and the acquired diopter scale.

17. A method of controlling an imaging apparatus for acquiring an image of an eye to be inspected on the basis of return light from the eye to be inspected irradiated with measuring light, the method comprising:
acquiring an image of an area of the eye to be inspected corresponding to a first area in an image of the eye to be inspected by lighting a fixation target at a first position; and changing, in a case where an image of an area of the eye to be inspected corresponding to a second area in an image of the eye to be inspected is acquired, the first position to a second position at which the fixation target is lighted, on the basis of a distance between the first area and the second area and a position of a focusing unit in an optical path when the fixation target is presented to the eye to be inspected through the focusing unit.

18. A method of controlling an imaging apparatus according to claim 17, further comprising the steps of:
   acquiring the diopter scale of the eye to be inspected on the basis of an in-focus state of the focusing unit in a case where the fixation target is presented to the eye to be inspected through the focusing unit; and
   acquiring the second position on the basis of the distance and the acquired diopter scale.

19. A recording medium having recorded thereon a program for causing a computer to perform the steps of the method of controlling an imaging apparatus according to claim 17.

* * * * *